United States Patent
Watson et al.

(10) Patent No.: US 9,236,227 B2
(45) Date of Patent: Jan. 12, 2016

(54) COLD PLASMA TREATMENT DEVICES AND ASSOCIATED METHODS

(75) Inventors: Gregory A. Watson, Sanford, FL (US); Marc C. Jacofsky, Phoenix, AZ (US)

(73) Assignee: Plasmology4, Inc., Scottsdale, AZ (US)

( * ) Notice: Subject to any disclaimer, the term of this patent is extended or adjusted under 35 U.S.C. 154(b) by 567 days.

(21) Appl. No.: 13/620,205

(22) Filed: Sep. 14, 2012

(65) Prior Publication Data
US 2013/0068226 A1 Mar. 21, 2013

Related U.S. Application Data

(60) Provisional application No. 61/535,250, filed on Sep. 15, 2011.

(51) Int. Cl.
*H01J 37/32* (2006.01)
*A61M 16/06* (2006.01)
(Continued)

(52) U.S. Cl.
CPC .......... *H01J 37/321* (2013.01); *A61L 2/00* (2013.01); *A61L 2/0094* (2013.01); *A61L 2/14* (2013.01); *A61M 15/02* (2013.01); *A61M 16/06* (2013.01); *A61M 16/12* (2013.01); *A61N 1/40* (2013.01);
(Continued)

(58) Field of Classification Search
CPC ...... A62B 18/02; A62B 18/025; A62B 18/04; A62B 18/045; A62B 18/06; A62B 18/08; A62B 19/00; A62B 19/02; A62B 21/00; A62B 23/00–23/06; A61M 16/06–16/0694; A61M 15/02; A61N 1/40; A61N 1/44; A61L 2/14; H05H 1/46; H05H 1/3406; H05H 1/2406; H01J 37/32348
See application file for complete search history.

(56) References Cited

U.S. PATENT DOCUMENTS 2,927,322 A 3/1960 Simon et al.
3,432,722 A 3/1969 Naydan et al.
(Continued)

FOREIGN PATENT DOCUMENTS

DE 10 2006 046 763 A1 4/2008
JP 2006-244938 9/2006
(Continued)

OTHER PUBLICATIONS

Fridman et al., "Comparison of Direct and Indirect Effects of Non-Thermal Atmospheric-Pressure Plasma on Bacteria," *Plasma Processl Polym.*, 4, 370-375, 6 pages, Wiley-VCH Verlag GmbH & Co. KGaA, Weinheim (2007).
(Continued)

*Primary Examiner* — Valerie L Skorupa
(74) *Attorney, Agent, or Firm* — Sterne, Kessler, Goldstein & Fox P.L.L.C.

(57) ABSTRACT

An inhalable cold plasma mask device for generation of a breathable cold plasma for delivery to a patient. A biocompatible gas is received in a dielectric barrier discharge (DBD) device that is energized by an electrode that receives energy from a pulsed source. The DBD device can be grounded by a grounding structure. A grounding screen can be used prior to inhalation of the cold plasma. The inhalable cold plasma mask device includes the use of a single-layer or a two-layer approach to its construction. The inhalable cold plasma mask device can have one or two DBD devices. Such a device and associated method can be used to treat upper respiratory tract infections, as well as reducing inflammation, sinus and esophageal polyps in both size and frequency of occurrence.

20 Claims, 12 Drawing Sheets

(51) Int. Cl.
| | |
|---|---|
| H05H 1/24 | (2006.01) |
| A61M 15/02 | (2006.01) |
| A61M 16/12 | (2006.01) |
| A61N 1/44 | (2006.01) |
| A61N 1/40 | (2006.01) |
| A61L 2/00 | (2006.01) |
| H05H 1/46 | (2006.01) |
| A61L 2/14 | (2006.01) |

(52) U.S. Cl.
CPC .............. *A61N 1/44* (2013.01); *H01J 37/3244* (2013.01); *H01J 37/3266* (2013.01); *H01J 37/32348* (2013.01); *H05H 1/2406* (2013.01); *H05H 1/46* (2013.01); *A61M 2202/025* (2013.01); *A61M 2202/0208* (2013.01); *H05H 2001/2412* (2013.01); *H05H 2001/466* (2013.01); *H05H 2001/4682* (2013.01); *H05H 2240/20* (2013.01); *H05H 2245/1225* (2013.01); *H05H 2277/10* (2013.01)

(56) References Cited

U.S. PATENT DOCUMENTS

| | | | |
|---|---|---|---|
| 3,487,414 A | 12/1969 | Booker | |
| 3,735,591 A | 5/1973 | Burkhart | |
| 4,088,926 A | 5/1978 | Fletcher et al. | |
| 4,365,622 A | 12/1982 | Harrison | |
| 4,380,320 A | 4/1983 | Hollstein et al. | |
| 4,422,013 A | 12/1983 | Turchi et al. | |
| 4,954,320 A * | 9/1990 | Birmingham et al. | 422/186.04 |
| 5,079,482 A | 1/1992 | Villecco et al. | |
| 5,216,330 A | 6/1993 | Ahonen | |
| 5,225,740 A | 7/1993 | Ohkawa | |
| 5,304,888 A | 4/1994 | Gesley et al. | |
| 5,381,789 A | 1/1995 | Marquardt | |
| 5,698,164 A | 12/1997 | Kishioka et al. | |
| 5,876,663 A | 3/1999 | Laroussi | |
| 5,883,470 A | 3/1999 | Hatakeyama et al. | |
| 5,909,086 A | 6/1999 | Kim et al. | |
| 5,961,772 A | 10/1999 | Selwyn | |
| 5,977,715 A | 11/1999 | Li et al. | |
| 6,060,027 A * | 5/2000 | Conrad et al. | 422/186.07 |
| 6,096,564 A | 8/2000 | Denes et al. | |
| 6,113,851 A | 9/2000 | Soloshenko et al. | |
| 6,204,605 B1 | 3/2001 | Laroussi et al. | |
| 6,225,593 B1 | 5/2001 | Howieson et al. | |
| 6,228,330 B1 | 5/2001 | Herrmann et al. | |
| 6,262,523 B1 | 7/2001 | Selwyn et al. | |
| 6,441,554 B1 | 8/2002 | Nam et al. | |
| 6,455,014 B1 | 9/2002 | Hammerstrom et al. | |
| 6,611,106 B2 | 8/2003 | Monkhorst et al. | |
| 6,667,007 B1 | 12/2003 | Schmidt | |
| 6,955,790 B2 * | 10/2005 | Castor et al. | 422/186.04 |
| 6,956,329 B2 | 10/2005 | Brooks et al. | |
| 6,958,063 B1 | 10/2005 | Soll et al. | |
| 6,969,487 B1 * | 11/2005 | Sias et al. | 422/28 |
| 7,006,874 B2 | 2/2006 | Knowlton et al. | |
| 7,011,790 B2 | 3/2006 | Ruan et al. | |
| 7,037,468 B2 | 5/2006 | Hammerstrom et al. | |
| 7,081,711 B2 | 7/2006 | Glidden et al. | |
| 7,094,314 B2 | 8/2006 | Kurunczi | |
| 1,925,553 A1 | 3/2007 | Crowe et al. | |
| 7,215,697 B2 | 5/2007 | Hill | |
| 7,271,363 B2 | 9/2007 | Lee et al. | |
| 7,300,436 B2 | 11/2007 | Penny et al. | |
| 7,608,839 B2 | 10/2009 | Coulombe et al. | |
| 7,633,231 B2 * | 12/2009 | Watson | 315/111.51 |
| 7,683,342 B2 | 3/2010 | Morfill et al. | |
| 7,691,101 B2 | 4/2010 | Davison et al. | |
| 7,719,200 B2 | 5/2010 | Laroussi | |
| 7,777,151 B2 | 8/2010 | Kuo | |
| 7,785,322 B2 | 8/2010 | Penny et al. | |
| 7,799,290 B2 | 9/2010 | Hammerstrom et al. | |
| 8,267,884 B1 | 9/2012 | Hicks | |
| 8,294,369 B1 | 10/2012 | Laroussi | |
| 8,460,283 B1 | 6/2013 | Laroussi et al. | |
| 2002/0129902 A1 | 9/2002 | Babayan et al. | |
| 2003/0222586 A1 | 12/2003 | Brooks et al. | |
| 2005/0088101 A1 | 4/2005 | Glidden et al. | |
| 2005/0179395 A1 | 8/2005 | Pai | |
| 2006/0189976 A1 | 8/2006 | Karni et al. | |
| 2008/0145553 A1 | 6/2008 | Boulos et al. | |
| 2008/0159925 A1 | 7/2008 | Shimizu et al. | |
| 2009/0188626 A1 | 7/2009 | Lu et al. | |
| 2010/0133979 A1 | 6/2010 | Lu | |
| 2010/0275950 A1 | 11/2010 | Mack et al. | |
| 2011/0022043 A1 | 1/2011 | Wandke et al. | |
| 2011/0040239 A1 * | 2/2011 | Schneider et al. | 604/25 |
| 2011/0042560 A1 | 2/2011 | Ouyang et al. | |
| 2011/0126828 A1 * | 6/2011 | Wu et al. | 128/201.25 |
| 2012/0100524 A1 | 4/2012 | Fridman et al. | |
| 2012/0187841 A1 | 7/2012 | Kindel et al. | |
| 2012/0259270 A1 | 10/2012 | Wandke et al. | |
| 2012/0282574 A1 * | 11/2012 | Holbeche | 433/216 |
| 2013/0022514 A1 | 1/2013 | Morfill et al. | |
| 2013/0053762 A1 | 2/2013 | Rontal et al. | |
| 2013/0064726 A1 * | 3/2013 | Morfill et al. | 422/186.21 |
| 2013/0134878 A1 | 5/2013 | Selwyn | |
| 2013/0199540 A1 | 8/2013 | Buske | |
| 2014/0000810 A1 | 1/2014 | Franklin et al. | |

FOREIGN PATENT DOCUMENTS

| | | |
|---|---|---|
| WO | WO 2005/084569 A1 | 9/2005 |
| WO | WO 2006/116252 | 11/2006 |
| WO | WO 2007/124910 A2 | 11/2007 |
| WO | WO 2010.107722 A1 | 9/2010 |
| WO | WO 2011/055368 A2 | 5/2011 |
| WO | WO 2011/055369 A2 | 5/2011 |
| WO | WO 2011/076193 A1 | 6/2011 |
| WO | WO 2012/106735 A2 | 8/2012 |
| WO | WO 2012/153332 A2 | 11/2012 |
| WO | WO 2013/101673 A1 | 7/2013 |

OTHER PUBLICATIONS

Alexander Fridman, "Plasma Chemistry," pp. 263-271, Cambridge University Press, 2008, 9 pages.

O'Connell et al., "The role of the relative voltage and phase for frequency coupling in a dual-frequency capacitively coupled plasma," *Applied Physics Letters*, 93 081502, 3 pages, American Institute of Physics (Aug. 25, 2008).

Nie et al., "A two-dimensional cold atmospheric plasma jet array for uniform treatment of large-area surfaces for plasma medicine," *New Journal of Physics*, 11 115015, 14 pages, IOP Publishing Ltd and Deutsche Physikalische Gesellschaft (2009).

Pompl et al., "The effect of low-temperature plasma on bacteria as observed by repeated AFM imaging," *New Journal of Physics*, 11 115023, 11 pages, IOP Publishing Ltd and Deutsche Physikalische Gesellschaft (Nov. 26, 2009).

Walsh et al., "Three distinct modes in a cold atmospheric pressure plasma jet," *J. Phys. D.: Appl. Phys.* 43 075201, 14 pages, IOP Publishing Ltd (Feb. 3, 2010).

Ricci et al., "The effect of stochastic electrical noise on hard-to-heal wounds," *Journal of Wound Care*, 8 pages, 19:3 Mark Allen Publishing Ltd ( Mar. 2010).

U.S. Appl. No. 61/485,747, filed May 13, 2011, inventor Thomas J. Sheperak, 14 pages.

Liu et al., "Sub-60° C. atmospheric helium-water plasma jets: modes, electron heating and downstream reaction chemistry," *J. Phys. D: Appl. Phys.* 44 345203, 13 pages, IOP Publishing Ltd. (Aug. 11, 2011).

Pei et al., "Inactivation of a 25.5 μm *Enterococcus faecalis* biofilm by a room-temperature, battery-operated, handheld air plasma jet," *J. Phys. D. Appl. Phys.*, 45 165205, 5 pages, IOP Publishing Ltd (Apr. 4, 2012).

Walsh et al., "Chaos in atmospheric-pressure plasma jets," *Plasma Sources Sci. Technol.*, 21 034008, 8 pages, IOP Publishing Ltd (May 2, 2012).

(56) References Cited

OTHER PUBLICATIONS

Banu, et al., "Cold Plasma as a Novel Food Processing Technology," *International Journal of Emerging trends in Engineering and Development*, Issue 2, vol. 4, ISSN 2249-6149, pp. 803-818, 16 pp. (May 2012).

Dobrynin, et al., "Live Pig Skin Tissue and Wound Toxicity of Cold Plasma Treatment," *Plasma Medicine*, 1(1):93-108, 16 pages, Begell House, Inc. (2011).

Fernández, et al., "The inactivation of *Salmonella* by cold atmosphere plasma treatment," *Food Research International*, 45:2, 678-684, 7 pages, Elsevier Ltd. (Mar. 2012).

Tien, et al., "The Bilayer Lipid Membrane (BLM) Under Electrical Fields," *IEEE Transactions on Dielectrics and Electrical Institute*, 10:5, 717-727, 11 pages (Oct. 2003).

Jayaram, et al.., "Optimization of Electroporation Waveforms for Cell Sterilization," *IEEE Transactions on Industry Applications*, 40:6, 1489-1497, 9 pages (2004).

Fridman, et al., "Use of Non-Thermal Atmospheric Pressure Plasma Discharge for Coagulation and Sterilization of Surface Wounds," *IEEE International Conference on Plasma Science*, Abstract, p. 257, 1 page (Jun. 2005).

Fridman, et al., "Use of Non-Thermal Atmospheric Pressure Plasma Discharge for Coagulation and Sterilization of Surface Wounds," 6 pages (Jun. 2005).

Fridman, et al., "Blood Coagulation and Living Tissue Sterilization by Floating-Electrode Dielectric Barrier Discharge in Air," *Plasma Chem Plasma Process*, 26: 425-442, 18 pages, Springer Science Business Media, Inc. (2006).

Gurol, et al., "Low Temperature Plasma for decontamination of *E. coli* in milk," *International Journal of Food Microbiology*, 157: 1-5, 5 pages, Elsevier B.V. (Jun. 2012).

Lado, et al., "Alternative food-preservation technologies: efficacy and mechanisms," *Microbes and Infection*, 4: 433-440 8 pages, Elsevier SAS (2002).

Leduc, et al., "Cell permeabilization using a non-thermal plasma," *New Journal of Physics*, 11: 115021, 12 pages, IOP Publishing Ltd and Deutsche Physikalische Gesellschaft (2009).

Machado, et al., "Moderate electric fields can inactivate *Escherichia coli* at room temperature," *Journal of Food Engineering*, 96: 520-527, 8 pages, Elsevier Ltd. (2009).

Li, et al., "Optimizing the distance for bacterial treatment using surface micro-discharge plasma," *New Journal of Physics*, 14: 023058, 11 pages, IOP Publishing Ltd and Deutsche Physikalische Gesellschaft (Feb. 2012).

Morfill, et al., "Nosocomial infections—a new approach towards preventive medicine using plasmas," *New Journal of Physics*, 11: 115019, 10 pages, IOP Publishing Ltd and Deutsche Physikalische Gesellschaft (2009).

Nian, et al., "Decontamination of *Salmonella* on Sliced Fruits and Vegetables Surfaces using a Direct-Current, Atmospheric-Pressure Cold Plasma," *IEEE International Conference on Plasma Science*, p. 1, 1 page (Jun. 2011).

Toepfl, et al., "High intensity pulsed electric fields applied for food preservation," *Chemical Engineering and Processing*, 46: 537-546, 10 pages, Elsevier B.V. (2007).

International Search Report mailed Nov. 30, 2012 for Appl. No. PCT/US2012/55615, 3 pages.

Written Opinion of International Searching Authority mailed Nov. 30, 2012, for Appl. No. PCT/US2012/55615, 3 pages.

English-language abstract for: Ryuichiro et al. JP 2006-244938, Sep. 14, 2006, 2 pages.

Dumé, Belle, "Cold Plasmas Destroy Bacteria," article, [online], [retrieved on Jan. 5, 2007], Retrieved from the PhysicsWeb website using Internet <URL:http://physicsweb.org/articles/news7/4/19>.

Gould, Phillip and Eyler, Edward, "Ultracold Plasmas Come of Age," article [online], [retrieved on Jan. 5, 2007], Retrieved from the PhysicsWeb website using Internet <URL:http://physicsweb.org/articles/world/14/3/3>.

Schultz, James, "Cold Plasma Ignites Hot Applications," article, [online], [retrieved on Jan. 5, 2007], Retrieved from the Old Dominion University website using Internet <URL:http://www.odu.edu/ao/instadv/quest/coldplasma.html>.

Lamba, Bikram, "Advent of Cold Plasma," article, [online], [retrieved on Jan. 5, 2007], Retrieved from the PhysOrg.com website using Internet <URL:http/www.physorg.com/printnews.php?newsid=6688>.

Book of Abstracts, 3rd International Conference on Plasma Medicine (ICPM-3), Sep. 19-24, 2010, International Society for Plasma Medicine.

International Search Report issued Aug. 6, 2008 for Appl. No. PCT/US2008/061240, 1 page.

Written Opinion of International Searching Authority issued Aug. 6, 2008 for Appl. No. PCT/US2008/061240, 6 pages.

Extended European Search Report issued Feb. 8, 2012 for European Patent Appl. No. EP08746627.2, 7 pages.

Pointu et al., "Nitrogen Atmospheric Pressure Post Discharges for Surface Biological Decontamination inside Small Diameter Tubes," *Plasma Process. Polym*. 5:559-568, Wiley-VCH Verlag GmbH & Co. KGaA, Weinheim (2008).

Chakravarthy et al., "Cold Spark Discharge Plasma Treatment of Inflammatory Bowel Disease in an Animal Model of Ulcerative Colitis," *Plasma Medicine* (1)1:3-19, Begell House, Inc. (2011).

The Supplementary European Search Report mailed Jan. 23, 2015 for Appl. No. PCT/US2012/055615, 7 pages.

English-language abstract for: Artmann, H., DE 10 2006 046 763 A1, Pub. Apr. 3, 2008.

* cited by examiner

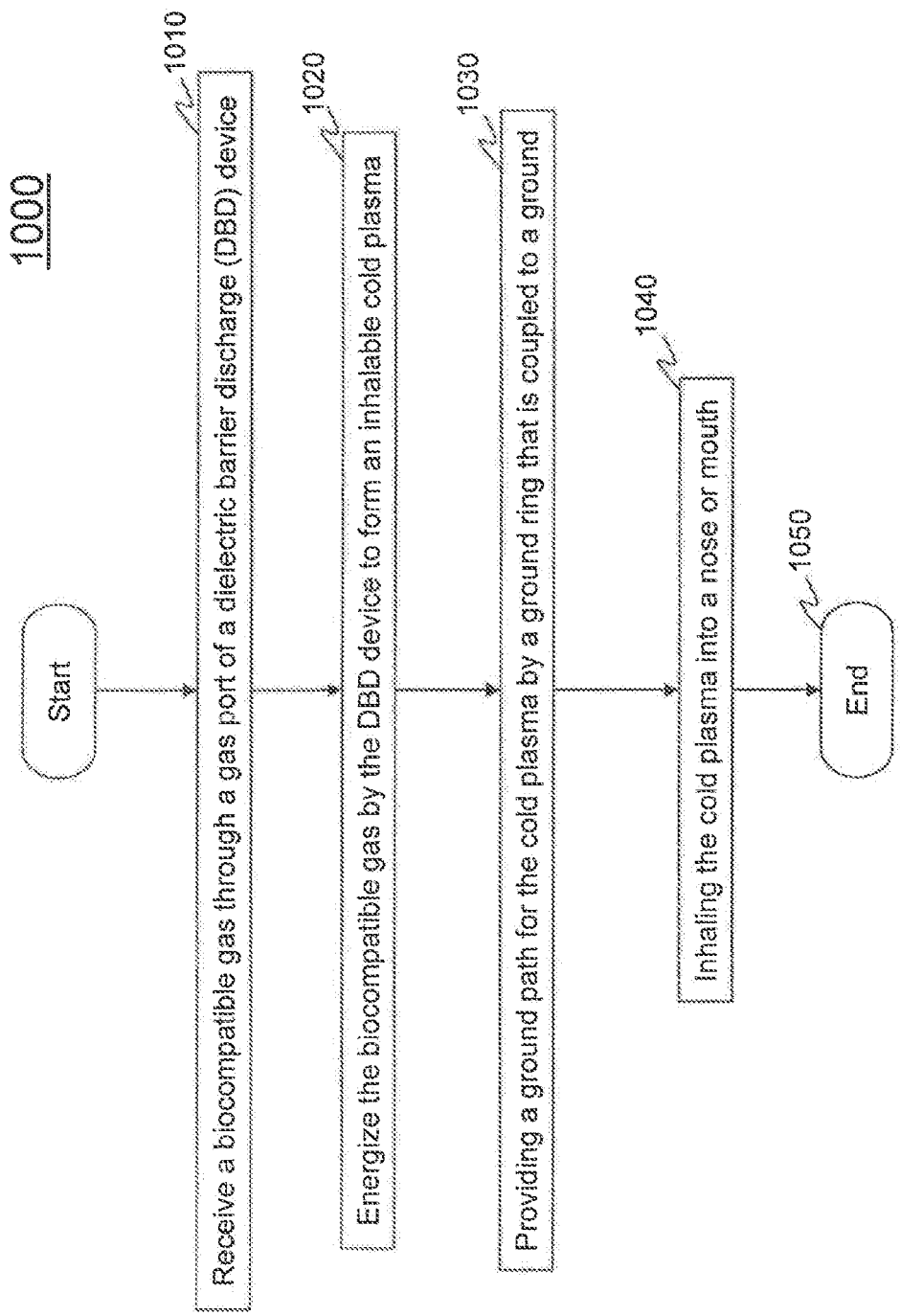

COLD PLASMA TREATMENT DEVICES AND ASSOCIATED METHODS

CROSS REFERENCE TO RELATED APPLICATIONS

The present application claims the benefit under 35 U.S.C. §119(e) of U.S. Provisional Patent Application No. 61/535,250, entitled "Harmonic Cold Plasma Devices and Associated Methods", filed on Sep. 15, 2011, which is hereby expressly incorporated by reference in its entirety.

This application is related to U.S. patent application Ser. No. 13/149,744, filed May 31, 2011, U.S. patent application Ser. No. 12/638,161, filed Dec. 15, 2009, U.S. patent application Ser. No. 12/038,159, filed Feb. 27, 2008, and U.S. Provisional Application No. 60/913,369, filed Apr. 23, 2007, each of which are herein incorporated by reference in their entireties.

BACKGROUND

1. Field of the Art

The present invention relates to devices and methods for creating cold plasmas, and, more particularly, to cold plasma treatment methods and application devices.

2. Background Art

Atmospheric pressure hot plasmas are known to exist in nature. For example, lightning is an example of a DC arc (hot) plasma. Many DC arc plasma applications have been achieved in various manufacturing processes, for example, for use in forming surface coatings. Atmospheric pressure cold plasma processes are also known in the art. Most of the at or near atmospheric pressure cold plasma processes are known to utilize positive to negative electrodes in different configurations, which release free electrons in a noble gas medium.

Respiratory ailments are a common and reoccurring problem for many people, with some form of coryza syndrome accounting for more physician visits in the United States than any other cause. Upper respiratory tract infections (URI's) are generally caused by the direct invasion of the inner lining (mucosa or mucus membrane) of the upper airway by the pathogenic microorganism. Acute pharyngitis accounts for 1-2% of all outpatient and emergency room visits, resulting in 7 million visits by adults alone. Approximately 20 million cases of acute sinusitis occur annually in the United States. One in three patients presenting an acute cough, about 12 million cases annually, are attributable to acute tracheobronchitis. The estimated annual economic impact of non-influenza-related upper respiratory infections is $40 billion. Chronic sinus infection, drug resistant tuberculosis, and cancers of the respiratory system present even greater treatment challenges, generally requiring surgical intervention and long-term therapies.

BRIEF SUMMARY OF THE INVENTION

An embodiment is described for an inhalable cold plasma mask device that has a mask layer conformal to a face, with the mask layer having an aperture. In the aperture is a dielectric barrier discharge (DBD) device, with the DBD device having a gas port, an electrode and a dielectric barrier, the gas port configured to receive gas, and the electrode coupled to a positive terminal for coupling to a cold plasma power supply. The DBD device also has a ground structure (e.g., ground ring), with the ground structure configured to be coupled to a ground.

Another embodiment is described of a method that receives a biocompatible gas through a gas port of a dielectric barrier discharge (DBD) device that is located within an aperture of a mask layer of a inhalable cold plasma mask device. The biocompatible gas is energized by the DBD device to form a cold plasma to be inhaled. The DBD device includes an electrode and a dielectric barrier, with the electrode coupled to a positive terminal for coupling to a cold plasma power supply. The DBD device is grounded by a ground ring disposed within the DBD device, with the ground ring coupled to a ground.

BRIEF DESCRIPTION OF THE DRAWINGS/FIGURES

Figure 6:
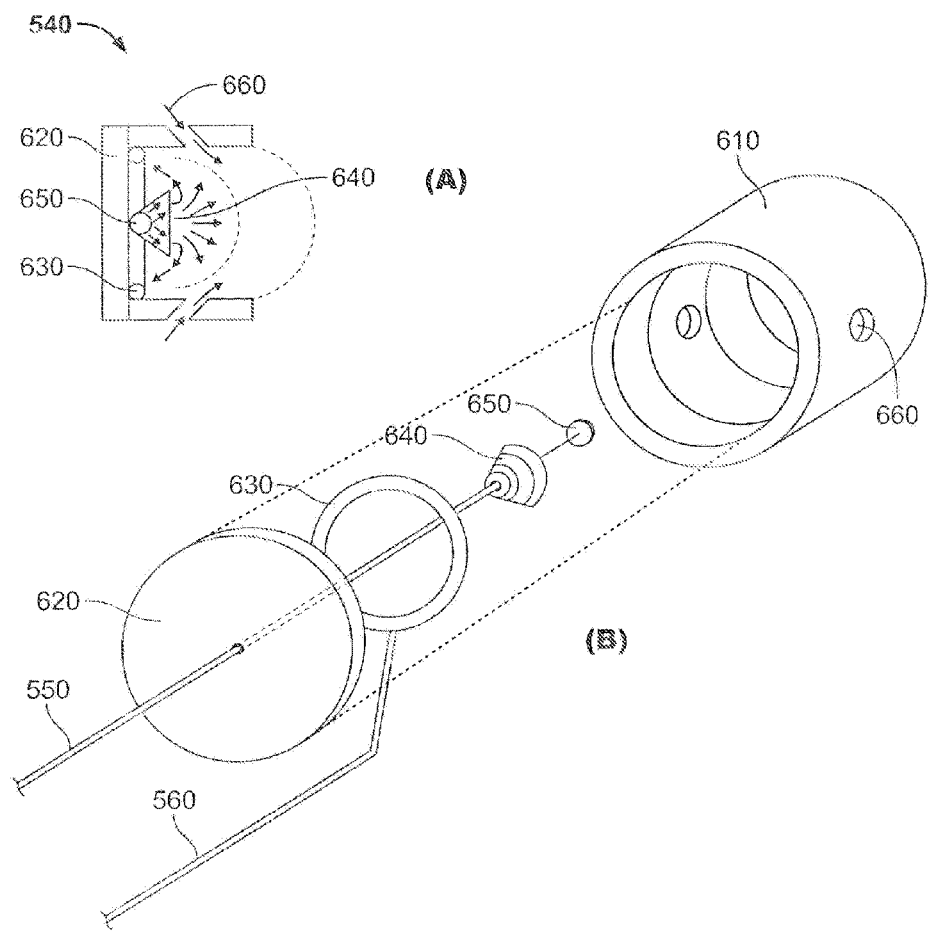

FIGS. 6A and 6B respectively illustrate a cross-sectional view and a detailed break-away view of the plasma generating module, in accordance with an embodiment of the present invention.

Figure 7:
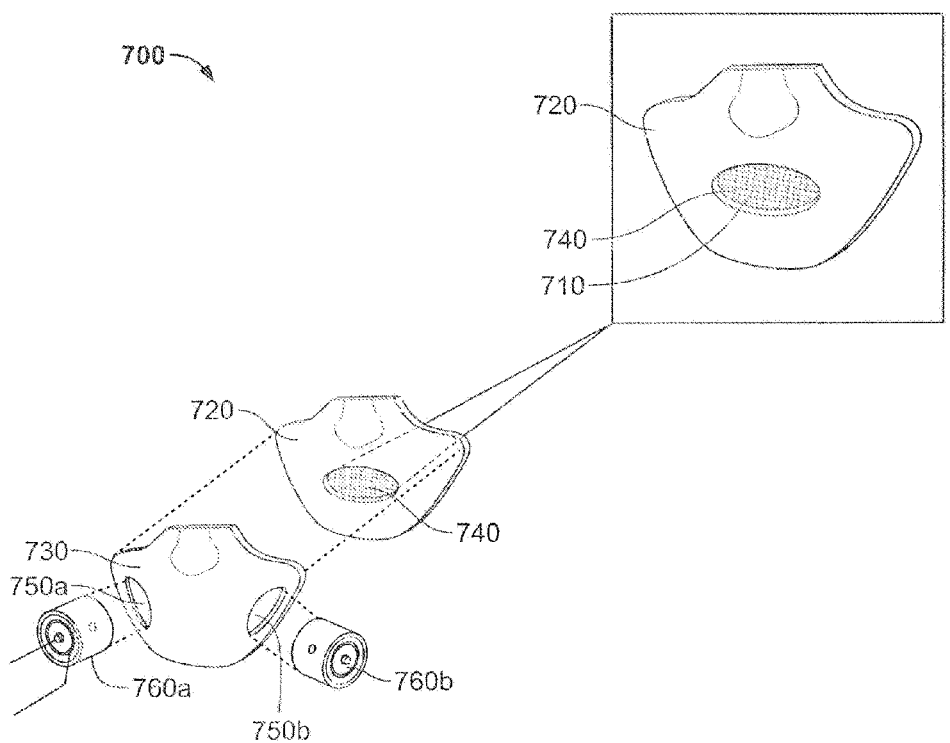

FIG. 7 illustrates a two-layer, twin-module embodiment of the cold plasma inhalable plasma mask device, in accordance with an embodiment of the present invention.

Figure 8:
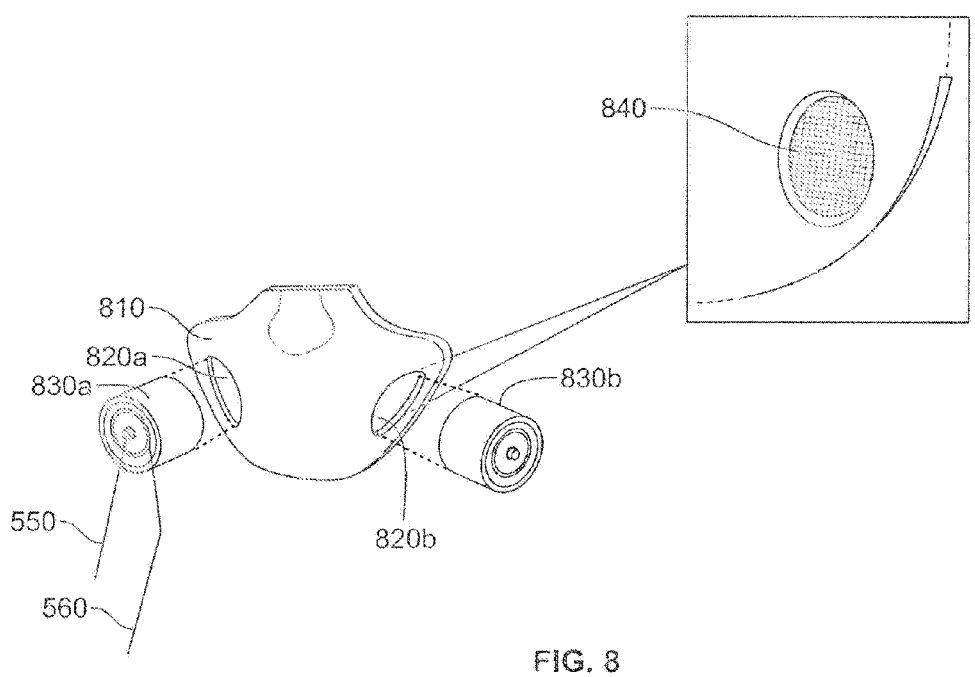

FIG. 8 illustrates a single layer, twin-module embodiment of the inhalable cold plasma mask device, in accordance with an embodiment of the present invention.

Figure 9:
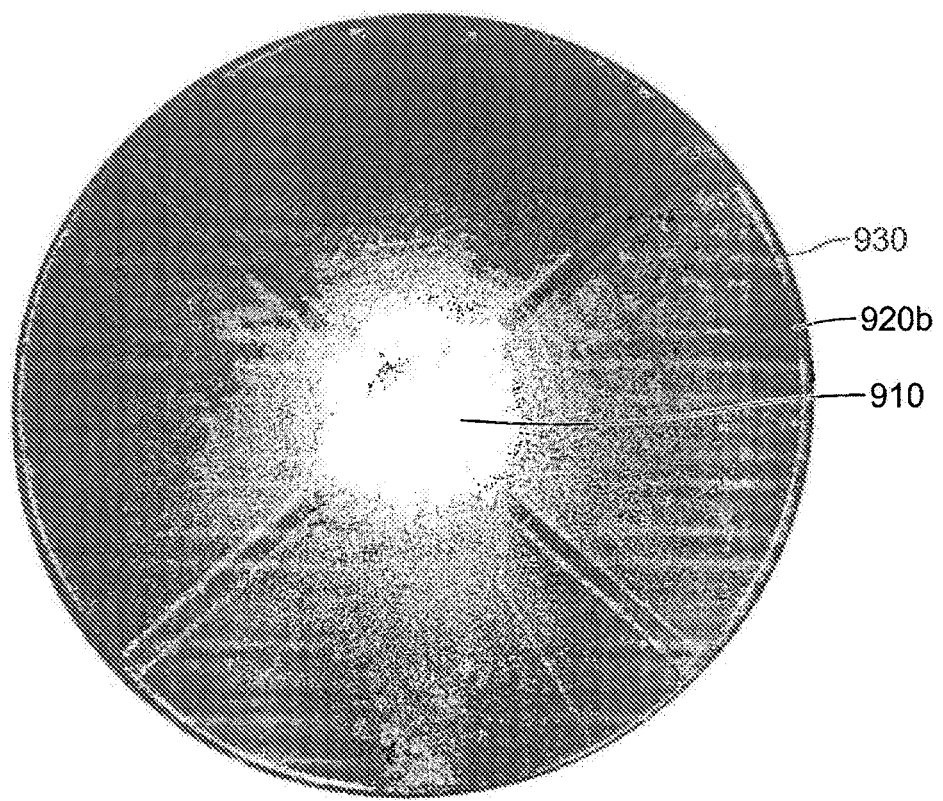

FIG. 9 illustrates a functioning inhalable cold plasma mask device, in accordance with an embodiment of the present invention.

FIG. 10 provides a method of using an inhalable cold plasma mask device, according to an embodiment of the present invention.

DETAILED DESCRIPTION OF THE INVENTION

Non-thermal atmospheric pressure plasmas have attracted a great deal of enthusiasm and interest by virtue of their provision of plasmas at relatively low gas temperatures. The provision of a plasma at such a temperature is of interest to a variety of applications, including wound healing, anti-infective processes, anti-tumorigenic effects, and various other medical therapies and sterilization.

Cold Plasma Application Device

Figure 1A:
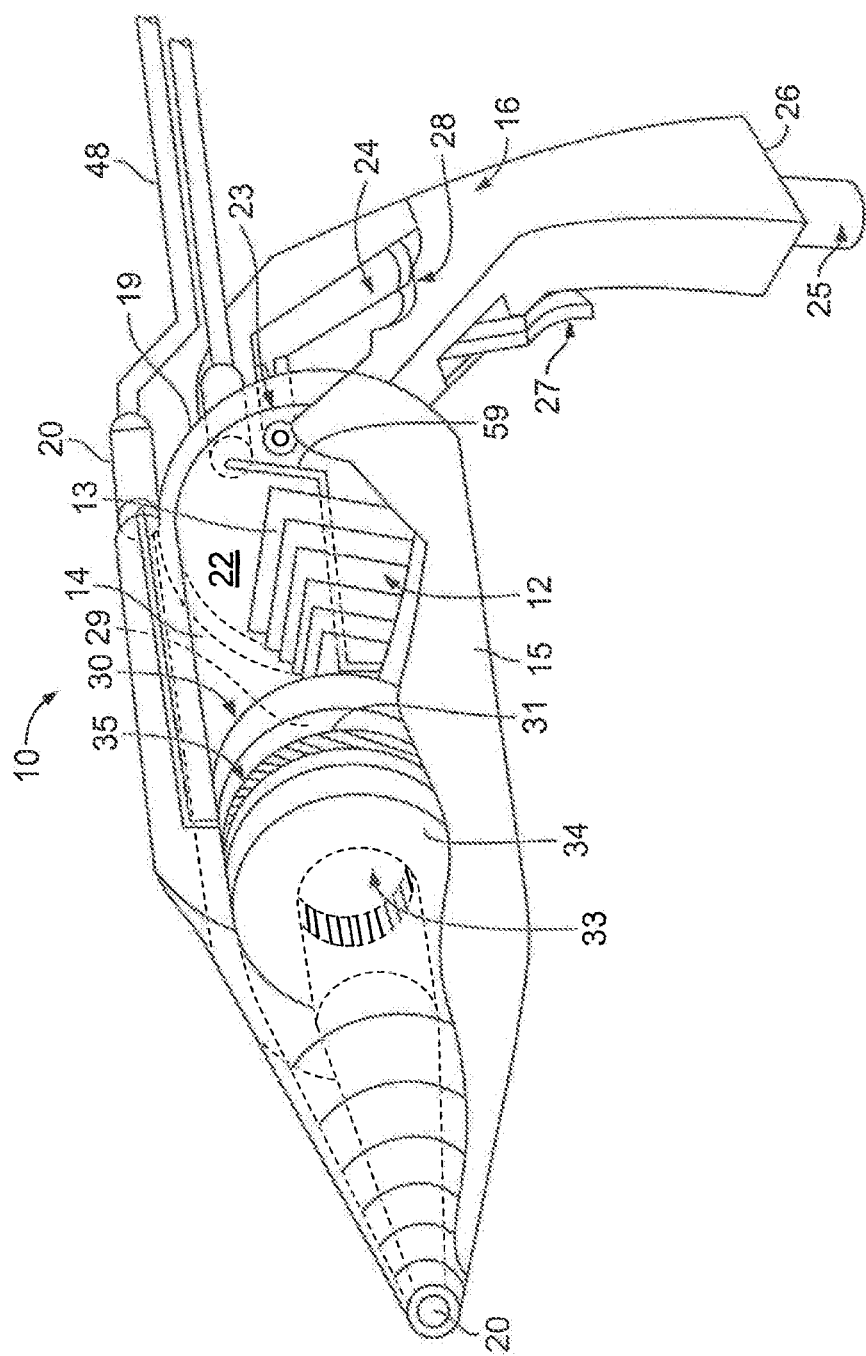
FIGS. 1A and 1B are cutaway views of the hand-held atmospheric harmonic cold plasma device, in accordance with embodiments of the present invention.

To achieve a cold plasma, a cold plasma device typically takes as input a source of appropriate gas and a source of high voltage electrical energy, and outputs a plasma plume. FIG. 1A illustrates such a cold plasma device. Previous work by the inventors in this research area has been described in U.S. Provisional Patent Application No. 60/913,369, U.S. Non-provisional application Ser. No. 12/038,159 (that has issued as U.S. Pat. No. 7,633,231) and the subsequent continuation applications (collectively "the '369 application family"). The following paragraphs discuss further the subject matter from this application family further, as well as additional developments in this field.

The '369 application family describes a cold plasma device that is supplied with helium gas, connected to a high voltage energy source, and which results in the output of a cold plasma. The temperature of the cold plasma is approximately 65-120 degrees F. (preferably 65-99 degrees F.), and details of the electrode, induction grid and magnet structures are described. The voltage waveforms in the device are illustrated at a typical operating point in '369 application family.

Figure 1B:
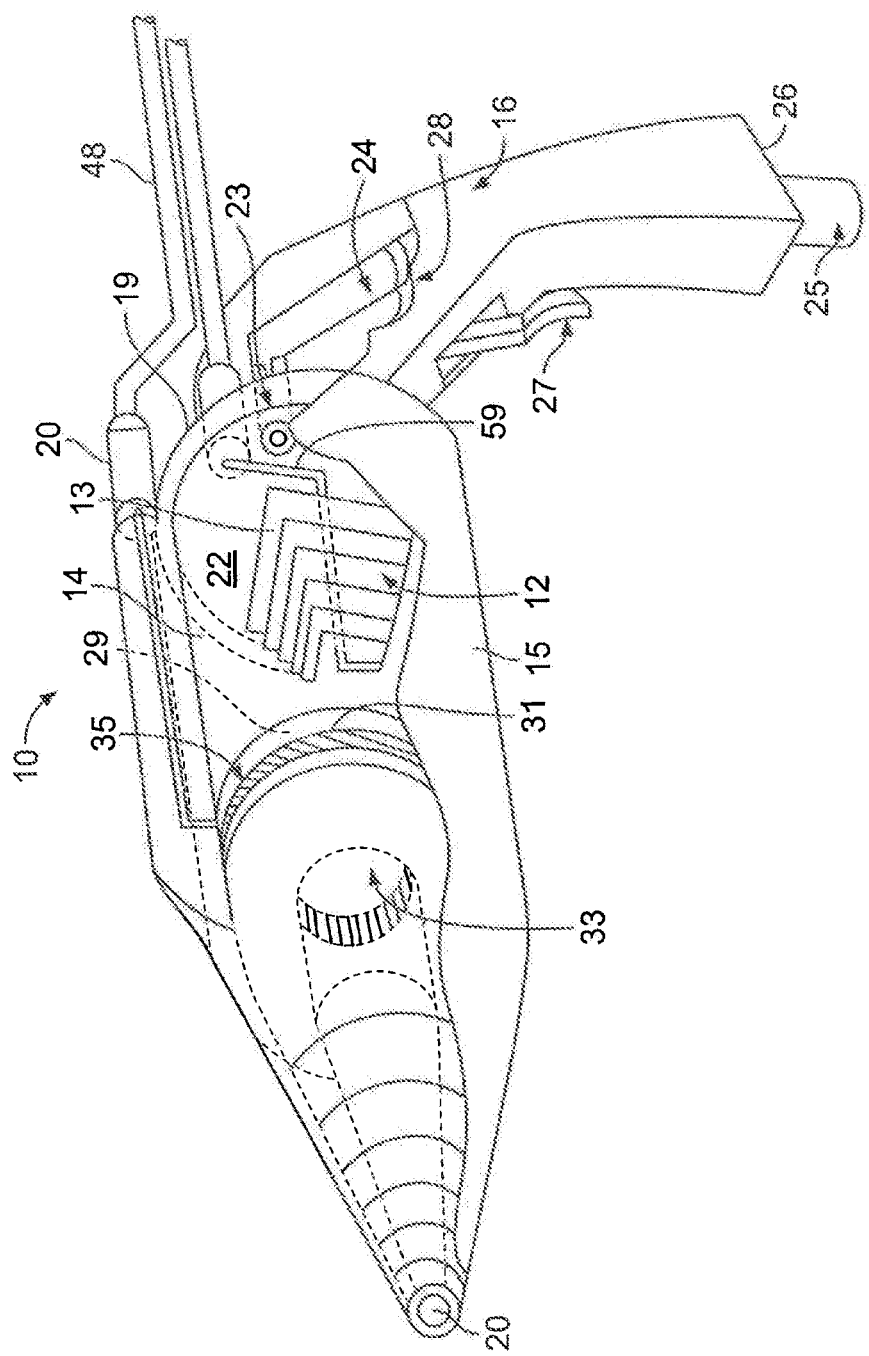
Figure 2A:
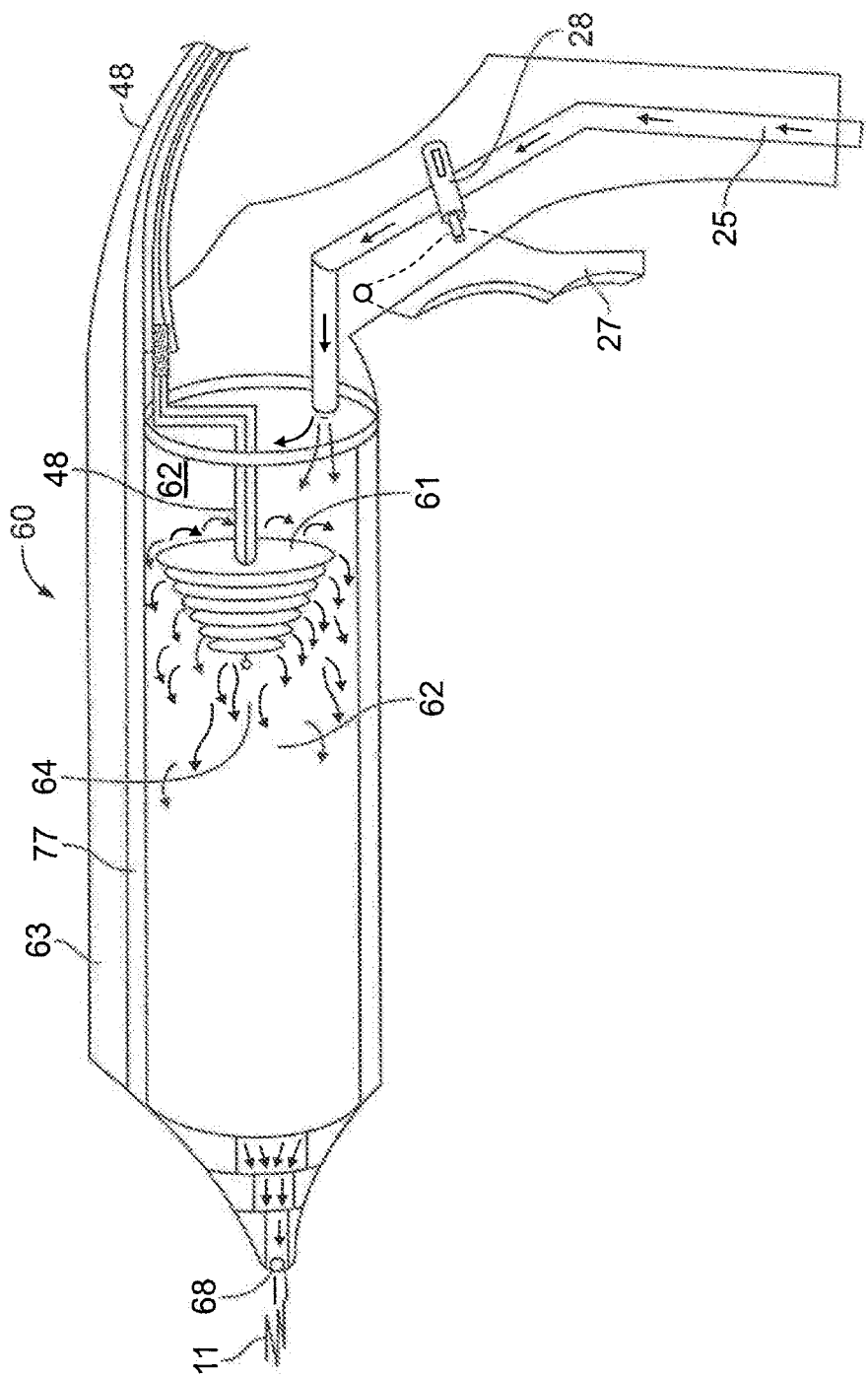
FIGS. 2A and 2B illustrate an embodiment of the cold plasma device without magnets, in accordance with embodiments of the present invention.
Figure 2B:
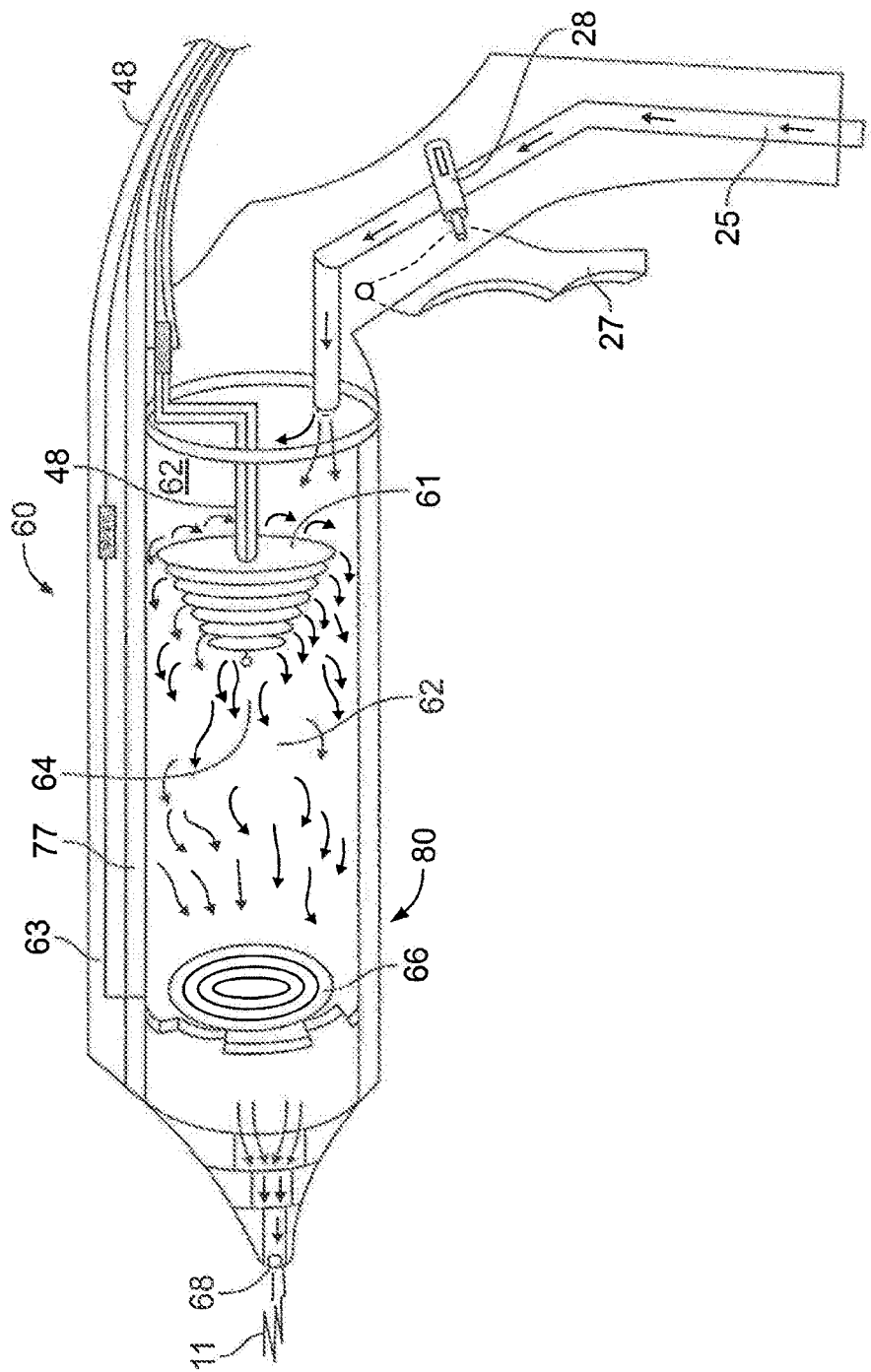

In a further embodiment to that described in the '369 application, plasma is generated using an apparatus without magnets, as illustrated in FIGS. 2A and 2B. In this magnet-free environment, the plasma generated by the action of the electrodes 61 is carried with the fluid flow downstream towards the nozzle 68. FIG. 2A illustrates a magnet-free embodiment in which no induction grid is used. FIG. 2B illustrates a magnet-free embodiment in which induction grid 66 is used. FIG. 1B illustrates the same embodiment as illustrated FIG. 2B, but from a different view. Although these embodiments illustrate the cold plasma is generated from electrode 12, other embodiments do not power the cold plasma device using electrode 12, but instead power the cold plasma device using induction grid 66.

In both a magnet and a magnet-free embodiment, the inductance grid 66 is optional. When inductance grid 66 is present, it provides ionization energy to the gas as the gas passes by. Thus, although the inductance grid 66 is optional, its presence enriches the resulting plasma.

As noted above, the inductance grid 66 is optional. When absent, the plasma will nevertheless transit the cold plasma device and exit at the nozzle 68, although in this case, there will be no additional ionization energy supplied to the gas as it transits the latter stage of the cold plasma device.

As noted with respect to other embodiments, magnetic fields can be used in conjunction with the production of cold plasmas. Where present, magnetic fields act, at least at some level, to constrain the plasma and to guide it through the device. In general, electrically charged particles tend to move along magnetic field lines in spiral trajectories.

As noted elsewhere, other embodiments can comprise magnets configured and arranged to produce various magnetic field configurations to suit various design considerations. For example, in one embodiment as described in the previously filed '369 application family, a pair of magnets may be configured to give rise to magnetic fields with opposing directions that act to confine the plasma near the inductance grid.

Cold Plasma Unipolar High Voltage Power Supply

The '369 application family also illustrates an embodiment of the unipolar high voltage power supply architecture and components used therein. The circuit architecture is reproduced here as FIG. 3, and this universal power unit provides electrical power for a variety of embodiments described further below. The architecture of this universal power unit includes a low voltage timer, followed by a preamplifier that feeds a lower step-up voltage transformer. The lower step-up voltage transformer in turn feeds a high frequency resonant inductor-capacitor (LC) circuit that is input to an upper step-up voltage transformer. The output of the upper step-up voltage transformer provides the output from the unipolar high voltage power supply.

Figure 3:
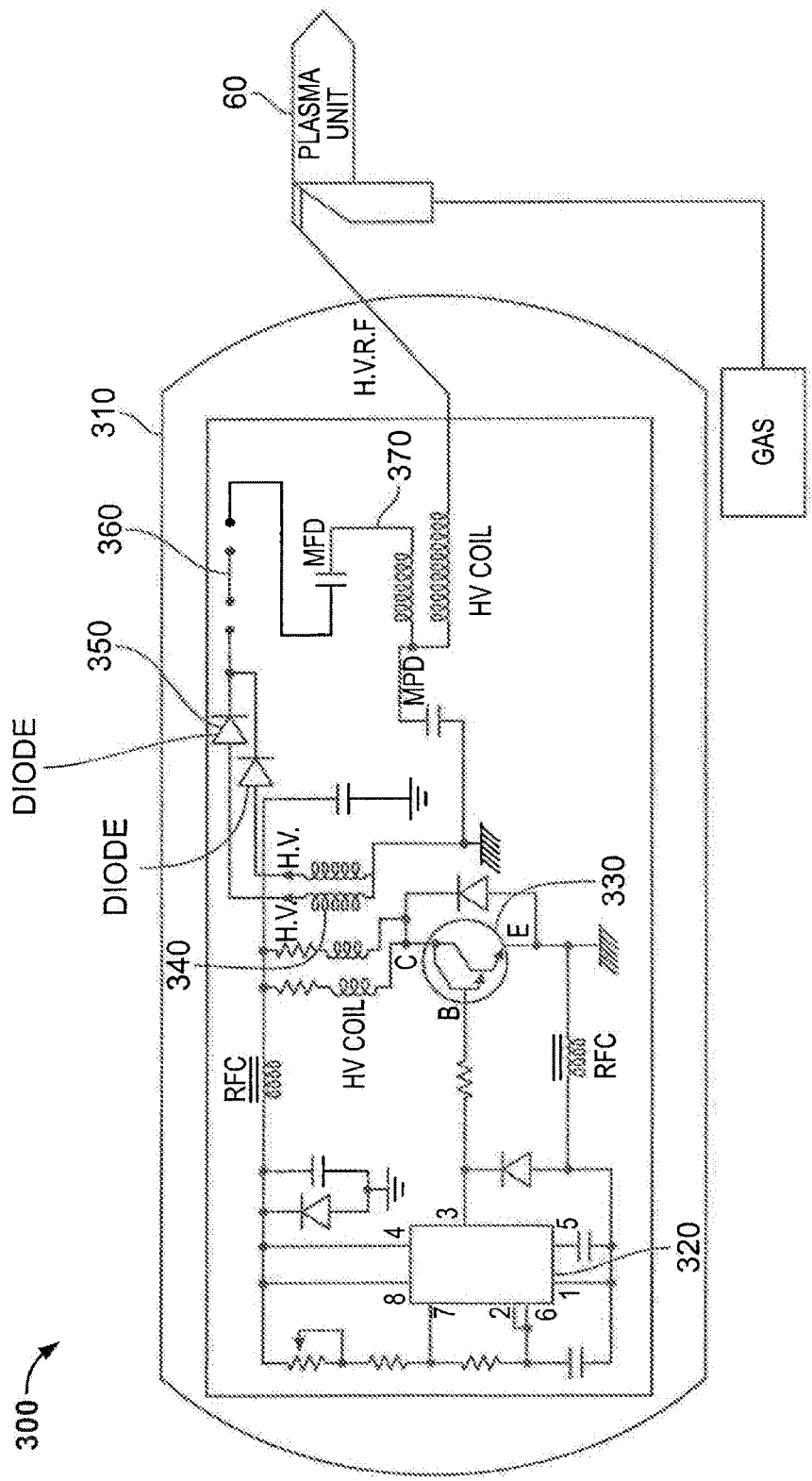
FIG. 3 is an exemplary circuit diagram of the power supply of a cold plasma device, in accordance with embodiments of the present invention.

FIG. 3 also illustrates an exemplary implementation of the unipolar high voltage power supply 310 architecture. In this implementation, a timer integrated circuit such as a 555 timer 320 provides a low voltage pulsed source with a frequency that is tunable over a frequency range centered at approximately 1 kHz. The output of the 555 timer 320 is fed into a preamplifier that is formed from a common emitter bipolar transistor 330 whose load is the primary winding of the lower step-up voltage transformer 340. The collector voltage of the transistor forms the output voltage that is input into the lower step-up voltage transformer. The lower step-up transformer provides a magnification of the voltage to the secondary windings. In turn, the output voltage of the lower step-up voltage transformer is forwarded to a series combination of a high voltage rectifier diode 350, a quenching gap 360 and finally to a series LC resonant circuit 370. As the voltage waveform rises, the rectifier diode conducts, but the quench gap voltage will not have exceeded its breakdown voltage. Accordingly, the quench gap is an open circuit, and therefore the capacitor in the series LC resonant circuit will charge up. Eventually, as the input voltage waveform increases, the voltage across the quench gap exceeds its breakdown voltage, and it arcs over and becomes a short circuit. At this time, the capacitor stops charging and begins to discharge. The energy stored in the capacitor is discharged via the tank circuit formed by the series LC connection.

Continuing to refer to FIG. 3, the inductor also forms the primary winding of the upper step-up voltage transformer 340. Thus, the voltage across the inductor of the LC circuit will resonate at the resonant frequency of the LC circuit 370, and in turn will be further stepped-up at the secondary winding of the upper step-up voltage transformer. The resonant frequency of the LC circuit 370 can be set to in the high kHz-low MHz range. The voltage at the secondary winding of the upper step-up transformer is connected to the output of the power supply unit for delivery to the cold plasma device. The typical output voltage is in the 10-150 kV voltage range. Thus, voltage pulses having a frequency in the high kHz-low MHz range can be generated with an adjustable repetition frequency in the 1 kHz range. The output waveform is shaped similar to the acoustic waveform generated by an impulse such as a bell is struck with a hammer. Here, the impulse is provided when the spark gap (or SCR) fires and produces the voltage pulse which causes the resonant circuits in the primary and secondary sides of the transformer to resonate at their specific resonant frequencies. The resonant frequencies of the primary and the secondary windings are different. As a result, the two signals mix and produce the unique 'harmonic' waveform seen in the transformer output. The net result of the unipolar high voltage power supply is the production of a high voltage waveform with a novel "electrical signature," which when combined with a noble gas or other suitable gas, produces a unique harmonic cold plasma that provides advantageous results in wound healing, bacterial removal and other applications.

The quenching gap 360 is a component of the unipolar high voltage power supply 310. It modulates the push/pull of electrical energy between the capacitance banks, with the resulting generation of electrical energy that is rich in harmonic content. The quenching gap can be accomplished in a number of different ways, including a sealed spark gap and an unsealed spark gap. The sealed spark gap is not adjustable, while unsealed spark gaps can be adjustable. A sealed spark gap can be realized using, for example, a DECI-ARC 3000 V gas tube from Reynolds Industries, Inc. Adjustable spark gaps provide the opportunity to adjust the output of the unipolar high voltage power supply and the intensity of the cold plasma device to which it is connected. In a further embodiment of the present invention that incorporates a sealed (and therefore non-adjustable) spark gap, thereby ensuring a stable plasma intensity.

In an exemplary embodiment of the unipolar high voltage power supply, a 555 timer 320 is used to provide a pulse repetition frequency of approximately 150-600 Hz. As discussed above, the unipolar high voltage power supply produces a series of spark gap discharge pulses based on the pulse repetition frequency. The spark gap discharge pulses have a very narrow pulse width due to the extremely rapid discharge of capacitive stored energy across the spark gap. Initial assessments of the pulse width of the spark gap discharge pulses indicate that the pulse width is approximately 1 nsec. The spark gap discharge pulse train can be described or modeled as a filtered pulse train. In particular, a simple resistor-inductor-capacitor (RLC) filter can be used to model the capacitor, high voltage coil and series resistance of the unipolar high voltage power supply. In one embodiment of the invention, the spark gap discharge pulse train can be modeled as a simple modeled RLC frequency response centered in the range of around 100 MHz. Based on the pulse repetition frequency of 192 Hz, straightforward signal analysis indicates that there would be approximately 2,000,000 individual harmonic components between DC and 400 MHz.

In another embodiment of the unipolar high voltage power supply described above, a 556 timer or any timer circuit can be used in place of the 555 timer 320. In comparison with the 555 timer, the 556 timer provides a wider frequency tuning range that results in greater stability and improved cadence of the unipolar high voltage power supply when used in conjunction with the cold plasma device.

Cold Plasma Treatments

Cold plasma treatment has been shown to be effective at greatly reducing bacterial loads, deactivating viruses, and causing apoptosis of tumorigenic cells after relatively short treatment times. In the cases where URI-causing pathogenic bacteria and viruses have infected body tissues, having a delivery device for supplying adequate non-thermal plasmas to the patient would prove useful in fighting off infections in the sinuses, bronchia, lungs, pharyngeal, and other esophageal tissues. Some common URI's that inhalable plasma would be effective at treating would be rhinitis, sinusitis, nasopharyngitis, pharyngitis, epiglottitus, laryngitis, laryngotracheitis, and tracheitis. Since cold plasma has also been demonstrated to reduce inflammation, inhalable plasma could show efficacy in the reduction of sinus and esophageal polyps in both size and frequency of occurrence.

It has been shown non-thermal plasma treatments are effective at reducing malignant tumors of human origin (pancreatic, glioblastoma, and prostate cancers) on the backs of nude mice. Non-thermal atmospheric plasma has been demonstrated to induce apoptosis, programmed cell death, in vitro. The selective apoptosis of cancerous cells in the presence of cold plasma may also provide a treatment modality for tumors of the respiratory and upper digestive tact.

The mechanisms of action for cold plasma are complex and not discrete and may differ for different pathogens and conditions. Reactive species of oxygen and nitrogen are one potential mechanism of action, as is ion bombardment, radio frequency, and electroporation. In order for these mechanisms to be effective within the respiratory tract, a cold plasma would need to be generated in close proximity to the mouth or nose in a manner that is easy to inhale into the lungs and safe for the patient. By generating cold plasma at the appropriate orifice at the time of inhalation, it would be possible for the patient to inhale highly charged ions and reactive species that remain therapeutic when they reach the lungs or surrounding tissues.

Cold Plasma Breathable Plasma Device

Figure 4:
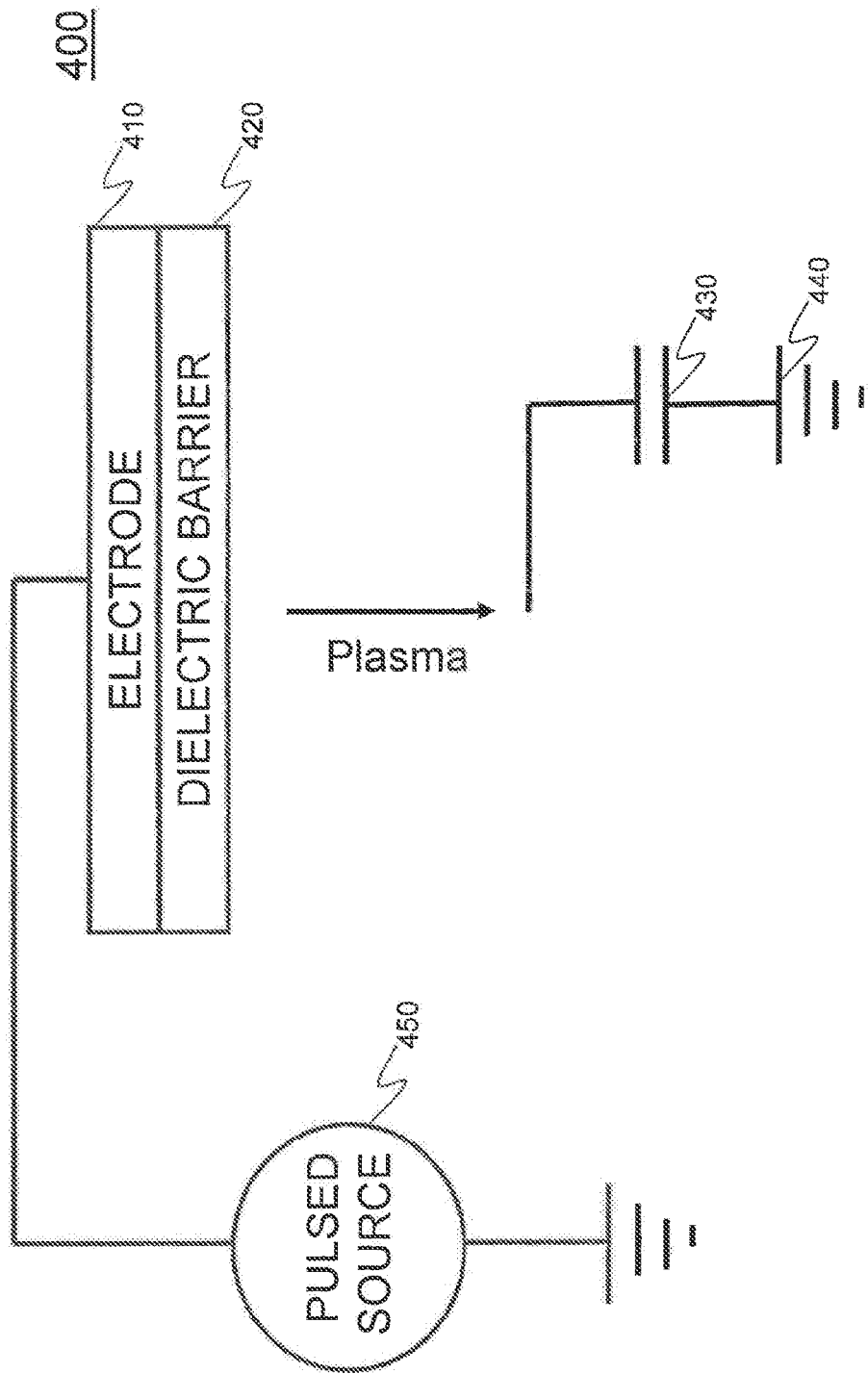
FIG. 4 illustrates the generation of cold plasma resulting from a dielectric barrier device, in accordance with embodiments of the present invention.

Devices, other than the cold plasma device illustrated above in FIG. 1, can also generate cold plasma. For example, cold plasma can also be generated by a dielectric barrier device, which relies on a different process to generate the cold plasma. As FIG. 4 illustrates, a dielectric barrier device (DBD) 400 contains one metal electrode 410 covered by a dielectric layer 420. The electrical return path 430 is formed by the ground 440 that can be provided by the subject undergoing the cold plasma treatment. Energy for the dielectric barrier device 400 can be provided by a power supply 450, such as that described above and illustrated in FIG. 2. More generally, energy is input to the dielectric barrier device in the form of pulsed electrical voltage to form the plasma discharge. By virtue of the dielectric layer, the discharge is separated from the metal electrode and electrode etching and gas heating are reduced. The pulsed electrical voltage can be varied in amplitude and frequency to achieve varying regimes of operation.

In exemplary embodiments, the DBD principle can be used to provide devices and methods for the application of cold plasma to one or more treatment areas of a patient. An inhalable cold plasma mask device would have a mask form, which receives an appropriate biocompatible or other suitable gas (e.g., air, helium-oxygen combinations, and the like), energizes the gas to form a cold plasma that is directed to the airways of a patient. Due to the inhalation, the energy of the cold plasma may be buffered in order to provide a lower energy cold plasma. In embodiments, the inhalable cold plasma mask device can have support points on the face of the patient to ensure that the device suitably mirrors the individual contours of the face of the particular patient, similar to a respirator. In further embodiments of the inhalable cold plasma mask device, individualized masks can be manufactured by obtaining a facial scan from which a custom mask can be developed for each patient.

Figure 5:
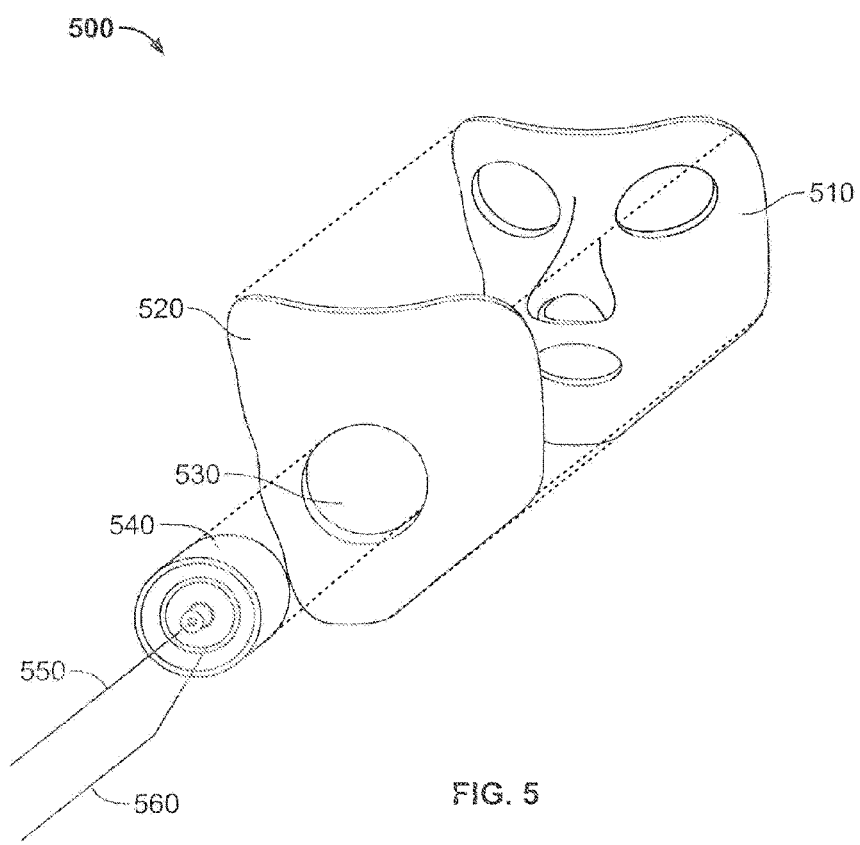
FIG. 5 illustrates a schematic view of an embodiment of the cold plasma inhalable plasma mask device, in accordance with an embodiment of the present invention.

FIG. 5 illustrates a schematic view of an embodiment of the inhalable cold plasma mask device 500. Inhalable cold plasma mask device 500 has an inner layer 510 with appropriate apertures for the nose and/or mouth of the patient. Inner layer 510 can be composed of clear acrylic material, or any other suitable material. Inhalable cold plasma mask device 500 also has an outer layer 520, which covers the lower portion (mouth and/or nose) of the face, while leaving the upper portion (e.g., eyes) of the face uncovered. Outer layer 520 can have a mouth/nose opening 530 that is compatible with the mouth/nose opening in inner layer 510. Like inner layer 510, outer layer 520 can be composed of clear acrylic material. Both inner layer 510 and outer layer 520 can cover only the mouth, only the nose, or the mouth and nose together. A plasma discharge module 540 is provided, which in an embodiment can be adapted to fit in mouth opening 530. Plasma discharge module 540 uses the DBD principle described above to generate the cold plasma. Plasma discharge module 540 receives energy from a positive power supply line 550 that can be connected to a cold plasma power supply, and a return path is provided by negative ground were 560. As noted above, in operation, the plasma generating module 540 is positioned in close proximity to the mouth of the patient. In operation, the cold plasma generated depends on both the pulsed voltage applied, as well as the gas used. The gas can be ambient air, a biocompatible gas, or the like. In other embodiments, gases other than ambient air can be supplied at the inbound side of the plasma generating module 540 to achieve an optimal or desired plasma chemistry for treatment or other useful purposes.

FIGS. 6A and 6B respectively illustrate a cross-sectional view and a detailed break-away view of the plasma generating module 540. Plasma generating module 540 has a module 610 that includes one or more air ports 660. Inside module 610 is a dielectric plate 620, ground ring 630, dielectric barrier 640 and electrode 650. Dielectric plate 620 can be made from any suitable dielectric material such as ceramic. PTFE, polyoxymethylene, polyamide-imides and the like. Ground ring 630 can be made from any metallic or suitably conductive material. Dielectric barrier 640 can be made from any suitable dielectric material such as ceramic, PTFE, polyoxymethylene, polyamide-imides and the like. Electrode 650 can be made from any suitable metallic material, such as brass and may be plated with one or more layers of exotic metals such as silver, nickel and/or gold. Positive power supply line 550 passes through dielectric plate 620, ground ring 630, dielectric barrier 640 and finally connects to electrode 650. Negative ground wire 560 is connected to ground ring 630. Dielectric barrier 640 can be a conical shape, although any shape falls within the scope of embodiments of the invention. In operation, electrode 650 is positively charged by the energy from a suitable cold plasma power supply source. As electrical energy flows out of dielectric barrier 640 seeking the negative ground ring 630, it charges the gas (e.g., ambient air) flowing through the air ports 660 in the side of the module 610 creating a coronal discharge that ionizes the gas (e.g., ambient air) mixture. Embodiments of the present invention are not limited to ambient air and could use a variety of suitable noble gas combinations. By way of example, a helium-oxygen mixture is suitable for breathing (heliox combination: 21% oxygen, 79% helium) and can be used without suffocation risk during the treatment. Nitrogen, argon, or other suitable gases could be introduced to control ion ratios and plasma chemistry to achieve the desired treatment effect.

FIG. 7 illustrates a two-layer, twin-module embodiment of the inhalable cold plasma mask device 700, together with the detail of an embodiment of the ground screen 740. Inhalable cold plasma mask device 700 includes inner layer 720 and outer layer 730. Inhalable cold plasma mask device 700 includes twin plasma discharge modules 760a, 760b that are disposed in openings 750a, 750b in outer layer 730. Inner layer 720 includes opening 710 that includes ground screen 740. Ground screen 740 is a safety device when there is a ground pathway included in plasma discharge modules 760a, 760b. Ground screen 740 ensures that no stray electricity is permitted to contact the face directly. In another embodiment, ground rings 630 could be eliminated from plasma discharge modules 760a, 760b, and ground screen 740 could be the preferred path to ground for the plasma power generating energy. This would drive the ions and plasma more directly toward the target orifice, e.g., the mouth or the nose of the patient.

FIG. 8 illustrates a single layer-, twin-module embodiment of the inhalable cold plasma mask device 800, together with detail of an embodiment of the ground screen 840. Inhalable cold plasma mask device 800 includes a single layer 810. Inhalable cold plasma mask device 800 includes twin plasma discharge modules 830a, 830b that are disposed in openings 820a, 820b in layer 810. Each opening 820a, 820b includes a ground screen 840. Ground screen 840 is a safety device when there is a ground included in the plasma discharge modules 830a, 830b. Ground screens 840 ensure that no stray electricity is permitted to contact the face directly. In another embodiment, ground rings 630 could be eliminated from plasma discharge modules 830a, 830b, and ground screens 840 could be the preferred path to ground for the plasma power generating energy. Equilibrium ambient air plasma discharge mask 800 is similar to equilibrium ambient air plasma discharge mask 700, but each plasma discharge module 830a, 830b has its own ground screen 840.

FIG. 9 illustrates a functioning inhalable cold plasma mask device having a cone-shaped acrylic dielectric barrier contained within air module creating an inhalable non-thermal plasma. The center portion 910 shows highly ionized gasses around the positively charged sphere. The fainter plasma 920 shows a consistent sheet of ionization along the acrylic cone leading back to the ground ring, which is the outermost ring 930.

Cold Plasma Inhalable Plasma Mask Usage Method

FIG. 10 provides a flowchart of an exemplary method 1100 to use a inhalable cold plasma mask device, according to an embodiment of the present invention.

The process begins at step 1010. In step 1010, a biocompatible gas is received through a gas port of a dielectric barrier discharge (DBD) device that is located within an aperture of a mask layer of a inhalable cold plasma mask device.

In step 1020, the biocompatible gas is energized by the DBD device to form a cold plasma to be inhaled, the DBD device further comprising an electrode and a dielectric Wirier, the electrode coupled to a positive wire that is in turn coupled to a cold plasma power supply.

In step 1030, the DBD device is grounded by a ground ring disposed within the DBD device, the ground ring being coupled to a ground.

In step 1040, inhaling the cold plasma through an orifice. In an embodiment, the orifice can be a mouth opening and/or a nose opening.

At step 1050, method 1000 ends.

It is to be appreciated that the Detailed Description section, and not the Summary and Abstract sections, is intended to be used to interpret the claims. The Summary and Abstract sections may set forth one or more but not all exemplary embodiments of the present invention as contemplated by the inventor(s), and thus, are not intended to limit the present invention and the appended claims in any way.

The present invention has been described above with the aid of functional building blocks illustrating the implementation of specified functions and relationships thereof. The boundaries of these functional building blocks have been arbitrarily defined herein for the convenience of the description. Alternate boundaries can be defined so long as the specified functions and relationships thereof are appropriately performed.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

What is claimed is:

1. An inhalable cold plasma mask device comprising:
   a mask layer adapted to conform to a face, the mask layer having an aperture;
   a dielectric barrier discharge (DBD) device disposed within the aperture, the DBD device having a gas port, an electrode and a dielectric barrier, the gas port configured to receive gas, and the electrode coupled to a positive wire; and
   a ground ring disposed within the DBD device, the ground ring configured to be coupled to a ground.

2. The inhalable cold plasma mask device of claim 1, further comprising:
   a ground screen placed in the aperture, the ground screen configured to be coupled to the ground.

3. The inhalable cold plasma mask device of claim 1, further comprising:
   a second mask layer configured to be located between the mask layer and the face, the second mask layer having a breathing aperture; and
   a ground screen placed in the breathing aperture, the ground screen configured to be coupled to the ground.

4. The inhalable cold plasma mask device of claim 1, wherein the mask layer further comprises a second aperture, and the inhalable cold plasma mask device further comprises:
   a second dielectric barrier discharge (DBD) device disposed within the second aperture, the second DBD device having a second gas port, a second electrode and a second dielectric barrier, the second gas port configured to receive gas, and the second electrode coupled to a second positive wire; and
   a second ground ring disposed within the second DBD device, the second ground ring, configured to be coupled to the ground.

5. The inhalable cold plasma mask device of claim 1, wherein the mask layer further comprises a second aperture, and the inhalable cold plasma mask device further comprises:
   a second dielectric barrier discharge (DBD) device disposed within the second aperture, the second DBD device having a second gas port, a second electrode and a second dielectric barrier, the second gas port configured to receive gas, and the second electrode coupled to a second positive wire;
   a second ground ring disposed within the second DBD device, the second ground ring configured to be coupled to the ground;
   a second mask layer configured to be located between the mask layer and the face, the second mask layer having, a breathing aperture; and
   a ground screen placed in the breathing aperture, the ground screen configured to be coupled to the ground.

6. The inhalable cold plasma mask device of claim 1, wherein the gas comprises air.

7. The inhalable cold plasma mask device of claim 1, wherein the gas comprises a helium-oxygen mixture.

8. The inhalable cold plasma mask device of claim 1, wherein the dielectric barrier is conically shaped.

9. The inhalable cold plasma mask device of claim 1, wherein the electrode comprises metallic material.

10. The inhalable cold plasma mask device of claim 1, wherein the dielectric barrier comprises at least one of ceramic, PTFE, polyoxymethylene and polyamide-imides.

11. A method comprising:
    receiving a biocompatible gas through a gas port of a dielectric barrier discharge (DBD) device disposed within an aperture of a mask layer of an inhalable cold plasma mask device;
    energizing the biocompatible gas by the DBD device to form a cold plasma to be inhaled, the DBI) device further comprising an electrode and a dielectric barrier, the electrode coupled to a positive wire being coupled to a cold plasma power supply; and
    grounding the DBD device by a ground ring disposed within the DBD device, the ground ring coupled to a ground.

12. The method of claim 11, wherein the energizing further includes using a ground screen placed in the aperture, the ground screen being coupled to the ground.

13. The method of claim 11, wherein the energizing further includes using a ground screen placed in a breathing aperture in a second mask layer configured to be located between the mask layer and a face, the ground screen being coupled to the ground.

14. The method of claim 11, wherein the energizing further includes using a second dielectric barrier discharge (DBD) device disposed within a second aperture, the second DBD device having a second gas port, a second electrode and a second dielectric barrier, the second gas port configured to receive gas, and the second electrode coupled to a second positive wire.

15. The method of claim 11, wherein the energizing further includes:
    using a second dielectric barrier discharge (DBD) device disposed within a second aperture, the second DBD device having a second gas port, a second electrode and a second dielectric barrier, the second gas port configured to receive gas, and the second electrode coupled to a second positive wire; and
    using a ground screen placed in a breathing aperture in a second mask layer configured to be located between the mask layer and a face, the ground screen configured to be coupled to the ground.

16. The method of claim 11, wherein the gas comprises air.

17. The method of claim 11, wherein the gas comprises a helium-oxygen mixture.

18. The method of claim 11, wherein the dielectric barrier is conically shaped.

19. The method of claim 11, wherein the electrode comprises metallic material.

20. The method of claim 11, wherein the dielectric barrier comprises at least one of ceramic, PTFE, polyoxymethylene and polyimide-imides.

* * * * *

UNITED STATES PATENT AND TRADEMARK OFFICE
CERTIFICATE OF CORRECTION

PATENT NO. : 9,236,227 B2
APPLICATION NO. : 13/620205
DATED : January 12, 2016
INVENTOR(S) : Watson et al.

It is certified that error appears in the above-identified patent and that said Letters Patent is hereby corrected as shown below:

Claims

Column 9, Line 33, claim 4, replace "the second ground ring, configured" with --the second ground ring configured--.

Column 10, Line 13, claim 11, replace "the DBI) device" with --the DBD device--.

Signed and Sealed this
Twelfth Day of April, 2016

Michelle K. Lee
*Director of the United States Patent and Trademark Office*